United States Patent [19]
Hauck et al.

[11] Patent Number: 5,318,597
[45] Date of Patent: Jun. 7, 1994

[54] RATE ADAPTIVE CARDIAC RHYTHM MANAGEMENT DEVICE CONTROL ALGORITHM USING TRANS-THORACIC VENTILATION

[75] Inventors: John A. Hauck, Shoreview; Arthur L. Olive, Stacy, both of Minn.

[73] Assignee: Cardiac Pacemakers, Inc., St. Paul, Minn.

[21] Appl. No.: 31,454

[22] Filed: Mar. 15, 1993

[51] Int. Cl.$^5$ ............................................ A61N 1/365
[52] U.S. Cl. ........................................................ 607/20
[58] Field of Search ............................. 607/17, 19, 20

[56] References Cited

U.S. PATENT DOCUMENTS

| | | | |
|---|---|---|---|
| 5,036,849 | 8/1991 | Hauck et al. | 607/9 |
| 5,074,303 | 12/1991 | Hauck | 607/9 |
| 5,137,019 | 8/1992 | Pederson et al. | 607/9 |

*Primary Examiner*—William E. Kamm
*Assistant Examiner*—Scott M. Getzow

*Attorney, Agent, or Firm*—Haugen and Nikolai

[57] ABSTRACT

A rate adaptive cardiac rhythm management device in which the pacing rate is adjusted in accordance with changes in the patient's minute ventilation. An adaptive four-pole elliptic digital filter, preferably implemented in software, functions to attenuate any signal components due to cardiac activity and motion from the minute ventilation signal over the range of breathing frequencies encountered in going from a sedentary state to active exercise. The pacemaker incorporates a microprocessor-based controller that is programmed to compute from peak-to-peak excursions of the sensed parameter the instantaneous tidal volume. Likewise, it computes, using a zero-crossing technique, the breathing interval. Knowing the breathing interval and the instantaneous tidal volume, it is possible to compute minute ventilation over a predetermined time interval and it is that factor that is employed in developing the ultimate control signal used to vary the stimulating rate between a lower rate limit and an upper rate limit.

9 Claims, 4 Drawing Sheets

RATE ADAPTIVE CARDIAC RHYTHM MANAGEMENT DEVICE CONTROL ALGORITHM USING TRANS-THORACIC VENTILATION

BACKGROUND OF THE INVENTION

I. Field of the Invention

This invention relates generally to implantable cardiac stimulating apparatus, and more particularly to a rate adaptive cardiac rhythm management device having a sensor for measuring trans-thoracic impedance variations and for deriving therefrom a control signal varying as a function of the patient's minute ventilation and which uses that control signal to adjust the rate at which it generates cardiac stimulating pulses to thereby accommodate the patient's physiologic demand.

II. Discussion of the Prior Art

The prior art is replete with patents which are designed to accommodate a patient's physiologic demand. In fact, there has been developed a whole class of implantable cardiac pacemakers which are referred to as being "rate adaptive", meaning that they do not merely generate cardiac stimulating pulses at a fixed, programmed rate irrespective of the patient's level of activity, but instead, operate to sense some parameter that correlates with metabolic need and then using the sensed signal, deriving a rate-controlling index for adjusting the pacing rate between a minimum or lower rate limit and a maximum or upper rate limit.

Parameters that have been sensed in the past include blood Ph, blood temperature, QT interval, blood oxygen saturation, respiratory rate, minute ventilation, etc. Specific control algorithms for developing the control signal based upon variations of the above parameters have each met with some problems. For example, where blood Ph is the parameter, sensor stability has been a problem. The Ph sensors used have been found to age and drift with time. Blood oxygen saturation can be measured using light emitters and sensors but they tend to complicate the lead system used to couple the pacemaker's pulse generator to the heart. Body temperature, on the other hand, while readily measured with a thermistor-type device, has proven to be a poor choice for use in a rate adaptive pacemaker because of the lag between the start of exercise and the detectable increase in blood temperature. Similarly, the use of ECG-based information, such as the pre-ejection period or the QT interval have not been entirely successful because of the difficulty in detecting the parameters in the presence of other myopotentials and motion artifacts typically involved.

Respiratory rate is also not a particularly suitable parameter on which the derivation of a rate control signal can be based. This is due to the fact that the correlation between heart rate and respiratory rate is not particularly strong or linear.

Another respiratory-related parameter that has been found to closely correlate with physical exercise and, therefore, metabolic demand is minute ventilation which may be defined as the volume of air inspired and expired during a predetermined time period. It has been found experimentally that minute ventilation (MV) tracks very well with metabolic need over a range of heart rates and, therefore, will provide a good index for a rate adaptive pacemaker, provided that the technique used to derive the MV signal is not contaminated by events other than respiratory activity.

It is known in the art that impedance plethysmography may be used to obtain an impedance vs. time analog signal that is modulated in accordance with the expansion and contraction of the thoracic cavity during inspiration and expiration. As is explained in the Pederson et al. Pat. No. 5,137,019, assigned to applicant's assignee, the impedance vs. time signal includes not only variations due to respiratory activity but due to cardiac activity and body motion as well. It is, therefore, desirable to isolate the information in the waveform relating to respiratory activity from that due to other causes. In the Hauck U.S. Pat. No. 5,074,303 entitled "Rate Adaptive Cardiac Pacer Incorporating Switched Capacitor Filter with Cut-Off Frequency Determined by Heart Rate", there is described an arrangement in which either systolic events or respiratory events can be selectively enhanced or attenuated by adjusting the analog filter parameters as a function of sensed heart rate. The present invention provides an alternative way for implementing the general concept disclosed in the Hauck Pat. No. 5,074,303 for effectively filtering out components in the Z vs. T waveform due to systolic function and motion artifacts over a range of heart rates and breathing rates which the patient would be expected to encounter in going from a sedentary state to a condition of vigorous exercise.

SUMMARY OF THE INVENTION

The adaptive rate cardiac rhythm management device constructed in accordance with the present invention includes a pacemaker housing adapted to be implanted subcutaneously in the chest area and it is connected by a suitable lead extending into the right ventricular chamber. Positioned on the distal end of the lead so as to be contained within the heart is a stimulating tip electrode and a more proximally located electrode in the form of a metal ring disposed on the lead body. An alternating current drive signal having a frequency of about 5 Khz and an amplitude which is sufficiently low to preclude capture is connected between the lead's tip electrode and the metal can comprising the pacemaker's housing. The ring electrode on the lead and an indifferent electrode disposed on the pacemaker's insulating lead socket are connected to a sense amplifier. Breathing activity as well as systolic events and other motion artifacts combine to modulate the alternating current carrier signal. The modulated carrier is fed into a demodulator whose output is an analog representation of the envelope which remains when the carrier is removed.

Contained within the device housing is an analog-to-digital converter which functions to sample the analog signal at a predetermined frequency and which then provides at its output a serial signal train of digital pulses which define the amplitude of the analog input at the sampling time.

The digital signal train is then applied as an input to a four-pole elliptic filter and decimator circuit. The filter and decimator is an adaptive filter having a plurality of weight sets which effectively establish the break frequencies for the adaptive filter. At any one time, only one weight set is applied and its values are dependent upon the current breathing rate and heart rate being sensed. For example, a low break frequency of $\frac{1}{2}$ Hz. is applicable during rest conditions providing a high degree of rejection of motion artifacts. Because the applicable filter break frequencies are related to both heart rate and breathing rate, it becomes possible to attenuate the higher frequency systolic contribution over the entire range from resting to full exercise.

The use of the adaptive filter also allows a peak detection algorithm to be used in determining tidal volume and ventilatory rate. The minute ventilation is, of course, the product of those two indices. In addition, the filter technique employed provides a significant rejection of artifacts not related to exercise, e.g., coughing, laughing or other transient events.

The algorithm controlling the operation of a microprocessor-paced controller disposed in the pacemaker housing includes a "sleep" mode which has the advantage of conserving battery power in the implanted device. In this mode, the system is periodically turned on for a time sufficient to determine whether a threshold is being exceeded, indicating exercise. If it is found to be above the threshold, the system remains on to perform the necessary processing to develop the control signal for modifying the pacing rate. If, however, a test shows that the minute ventilation is below the threshold, the electronics is shut back off for a predetermined time interval.

DESCRIPTION OF THE DRAWINGS

The foregoing features, advantages and objects will become apparent to those skilled in the art from the following detailed description of a preferred embodiment, especially when considered in conjunction with the accompanying drawings in which.

DESCRIPTION OF THE PREFERRED EMBODIMENT

The present invention may find application in a variety of implantable cardiac rhythm management devices, including bradycardia pacers, antitachycardia pacers and defibrillators, but for purposes of explanation, will be described in connection with a rate adaptive cardiac pacemaker.

Figure 1:
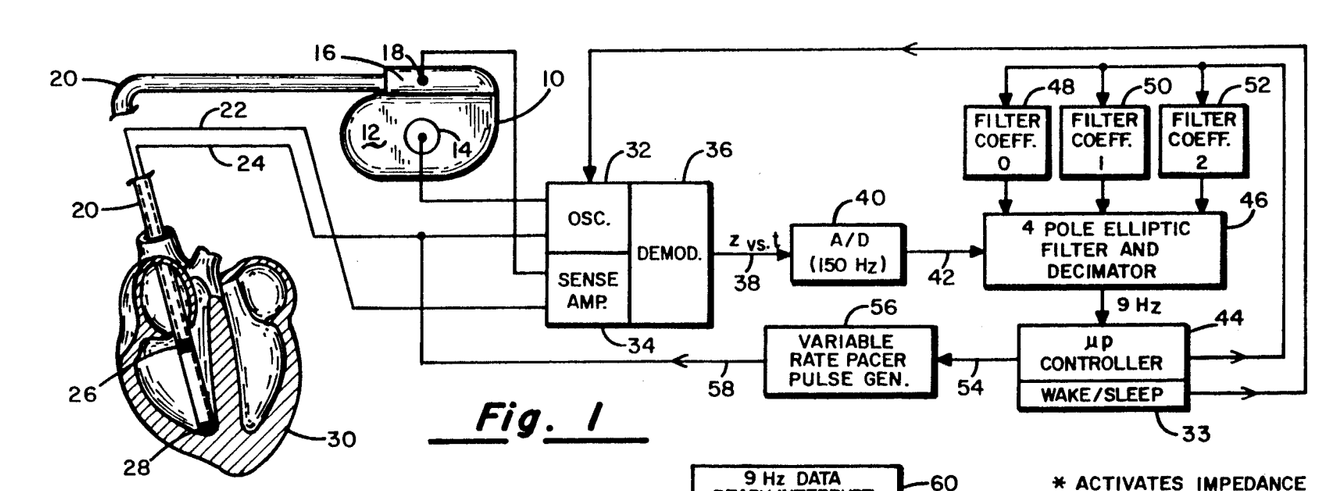
FIG. 1 is a block diagram depicting the preferred embodiment of the invention.

Referring first to FIG. 1, there is shown an implantable cardiac pacemaker 10 comprising a hermetically sealed container or housing 12 which is formed from metal, e.g., titanium, and which is covered over its entire surface except for a window 14 by a suitable insulating covering such as silicon rubber. Mounting atop the housing 12 is a molded plastic lead connector 16 having an indifferent metal electrode 18 disposed thereon.

The pacing lead itself is identified by numeral 20 and includes a plurality of conductors 22 and 24 extending the length thereof with conductor 22 terminating at a ring electrode 26 and the conductor 24 terminating at a distal tip electrode 28. The spacing between the electrodes 26 and 28 is such that when the lead is positioned with the tip electrode 28 at the apex of the right ventricle of the heart 30, the ring electrode 26 will be disposed within the blood pool within the heart.

The oscillator 32 is connected in driving relationship between the metal can surface 14 of the pacemaker 10 and the stimulating electrode 28. The frequency and amplitude of this drive signal is such that capture of the heart does not occur. Instead, it injects a high frequency carrier signal which is modulated by respiratory activity and physical motion of the patient, and the resulting modulated signal is detected between the electrode 26 and the indifferent electrode 18. These two electrodes feed into a sense amplifier 34. Because the indifferent electrode 18 is located subcutaneously proximate the pectoral muscles on the chest while the electrode 26 is disposed within the heart, the resulting modulation has a major component attributable respiratory activity. The arrangement of the electrodes to the drive source and sense amplifier is similar to that disclosed in the Hauck et al. U.S. Pat. No. 5,036,849 entitled "VARIABLE RATE CARDIAC PACER".

The output from the sense amplifier 34 is fed into a demodulator circuit 36 which functions to remove the high frequency carrier and leaving only the modulation envelope for further signal processing. This envelope is the Z vs. t analog signal which is fed over line 38 to an analog to digital converter 40. The A/D converter 40 may typically sample the analog signal on line 38 at a frequency of about 150 Hz and will produce a digital signal frame on its output line 42 with the digital signals representing the amplitude of the analog signal at each sampling time.

The oscillator 32 does not run continuously but, instead, is controlled by a wake/sleep control circuit 33 which is a part of the microprocessor controller 44.

The output of the A/D converter 40 is applied to a four-pole elliptic filter and decimator circuit 46 whose filter coefficients or sets of weights 48, 50 and 52 are computed by the microprocessor controller 44 as a function of detected breathing rate and heart rate, all as will be more fully described hereinbelow when the software flow diagram defining the algorithm executed by the microprocessor controller 44 is explained. While the four-pole elliptic filter and decimator 46 is illustrated as a separate circuit block in the diagram of FIG. I, those skilled in the art will appreciate that, being a digital filter, it is preferably implemented in software executed by the microprocessor-based controller 44 and typically would not be a discrete circuit.

Figure 2:
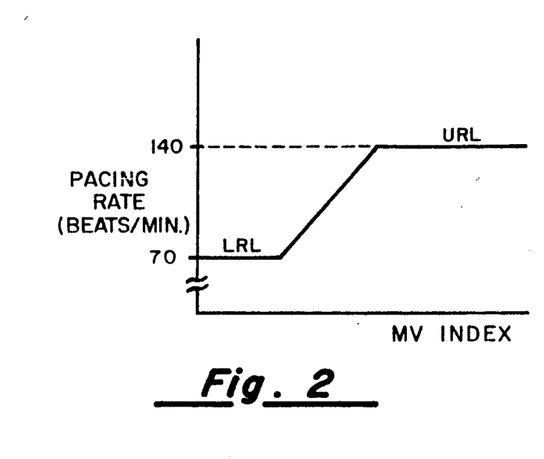
FIG. 2 is graph illustrating the variation in pacing rate with changes in minute ventilation.

The decimator function takes the 150 Hz sample rate of the A/D convertor 40 and reduces the rate at which sample points are accepted and processed by the microprocessor controller 44 to a much lower frequency, e.g., 9 Hz. These sample points are processed in accordance with the algorithm yet to be described so as to produce on the line 54 a control signal which varies in accordance with the patient's minute ventilation. This control signal, when applied to the variable rate pacemaker pulse generator 56 adjusts the rate at which cardiac stimulating pulses are produced at its output 58 for application to the stimulating electrode 28 at the distal end of the pacemaker lead 20. In this fashion, the electrical stimulating pulses would be produced at a rate which varies with changes in minute ventilation between a lower rate limit (LRL) and an upper rate limit (URL) as depicted in the graph of FIG. 2. All of the components identified by the reference numerals 32 through 56 are housed in the housing 12.

Figure 3:
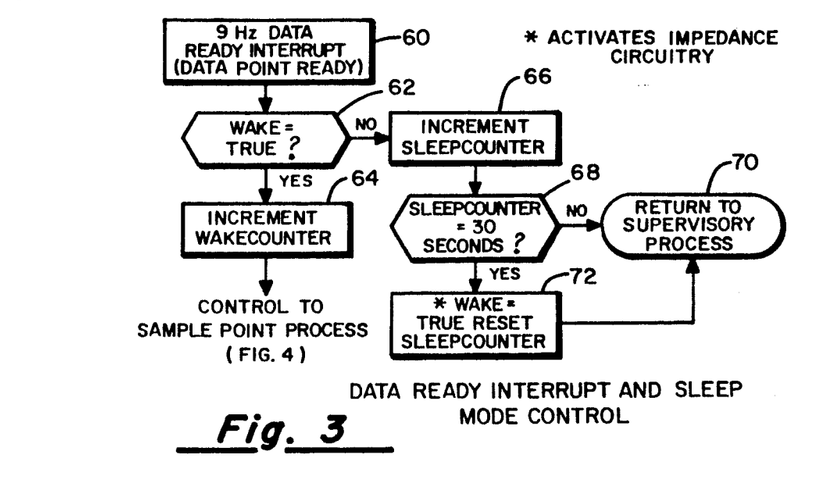
FIG. 3 is a software flow diagram illustrating the wake/sleep function.

Having described the overall configuration of the pacemaker constructed in accordance with the present invention, consideration will next be given to the operation thereof and, in this regard, attention is directed to the software diagram of FIG. 3 which indicates the operational features of the wake/sleep function 33 forming a part of the microprocessor controller 44 in FIG. 1.

Figures 4, 4A:
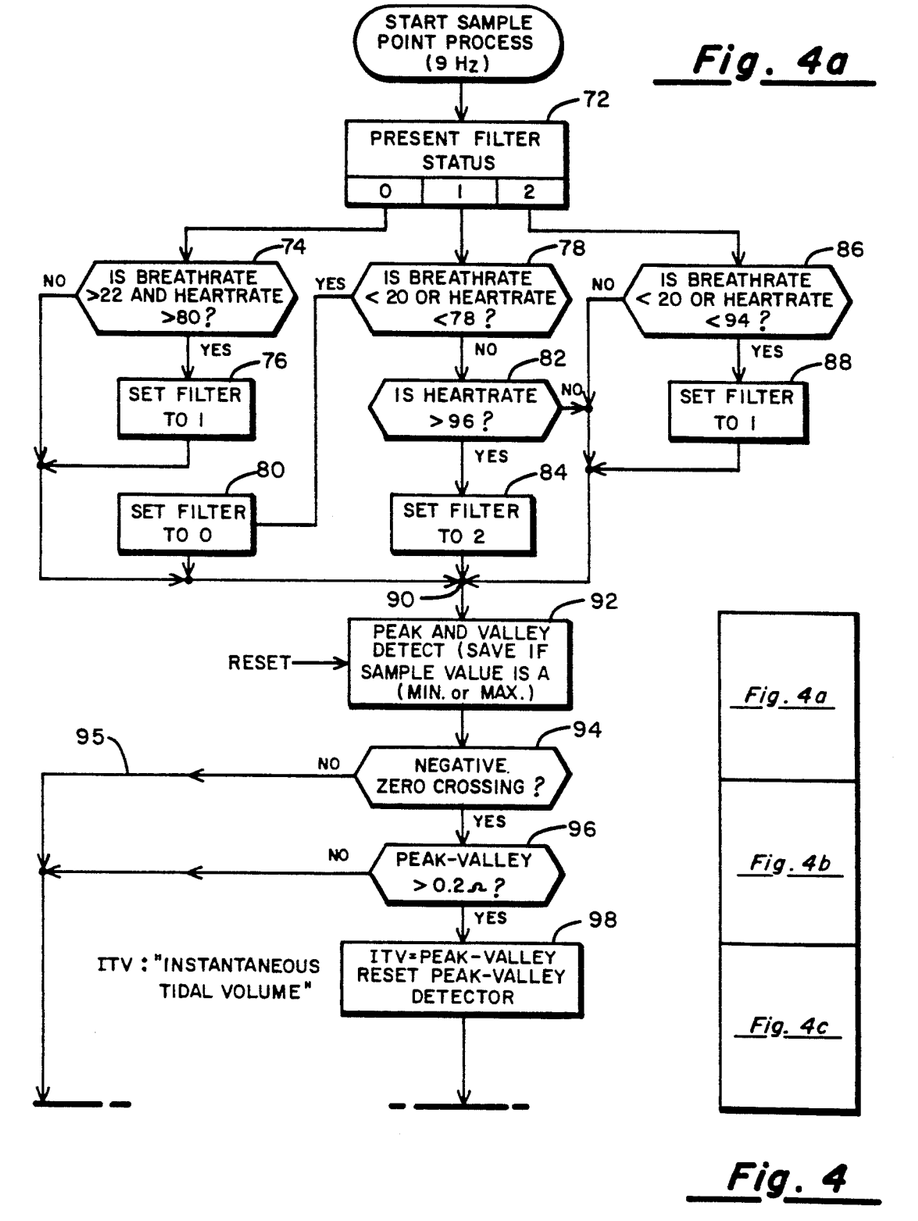
FIGS. 4A, 4B and 4C when arranged as in FIG. 4 is software flow diagram depicting the software algorithm employed by the microprocessor controller illustrated in FIG. 1 for developing the minute ventilation index.

The 9 Hz data sample point signal causes the microprocessor to issue a data ready interrupt 60 at the indicated rate and a test is then made (block 62) to determine whether a wake flag is true. If it is, a counter within the microprocessor 44 designated the "wake counter" is incremented (block 64) and the sample point process depicted by the flow diagram of FIG. 4 is entered. If, on the other hand, the test at block 62 reveals that the wake flag is false, the sleep counter is incremented (block 66). Then, a further test is made as represented by block 68 to determine whether the sleep counter has reached an arbitrarily set value such as 30 seconds. If not, no action is taken except that control returns to the supervisory process as indicated by block 70. If the sleep counter or timer had indicated that 30 seconds had elapsed since the sleep mode was first entered, the wake flag would be set to true and the sleep counter is reset to its "0" state (block 72) before control returns to the supervisory process. The impedance sensing circuitry, including oscillator 32, sense amplifier 34 and demodulator 36, is active only when the wake flag is set to its true state. Otherwise, it is inactive which, of course, conserves battery power.

Referring now to FIG. 4A, upon receipt of each sample point at the 9 Hz rate from the 4-pole elliptic filter and decimator 46, the then-present filter status, which indicate the operative set of filter weights is updated (block 72). If the present filter status were "0", the test indicated by decision block 74 is made to determine whether the average breath rate taken over a predetermined number of breathing cycles is greater than 22 per minute and whether the heart rate, also taken over a predetermined number of beats, is greater than 80 (block 74). If these two conditions are found to be true, the operative filter weight set is changed from "0" to "1" (block 76). If not, it remains at "0". Likewise, if the present filter status were a "1" (block 72), the test made at 78 is carried out to determine whether the average breath rate is less than 20 or the heart rate is less than 78. If either of these conditions is true, the filter weight set is set to a "0" (block 80). If the test made at decision block 78 is negative, a test is made to determine whether the heart rate exceeds 96 beats-per-minute (block 82) and if it does, the filter weight is set to its "2" status (block 84). Finally, if the present filter status were a "2" and the test made at decision block 86 shows that the average breath rate is less than 20 or the heart rate is less than 94, the filter weight is set to a "1" (block 88).

Each of the three filter weight sets implements a different break frequency in the four-pole elliptic filter 46. For example, in implementing the present invention, a filter setting of "0" may correspond to a filter break frequency of ½ Hz which is appropriate to effect a breath rate roll-off at 30 breaths-per-minute. A filter setting of "1" corresponds to 0.75 Hz which results in a breath rate roll-off of 45 breaths-per-minute. Filter setting "2" corresponds to a 1.0 Hz break frequency for a breath rate roll-off of 60 breaths-per-minute.

Irrespective of which of the above three paths is followed in updating the filter setting, control ultimately reaches junction 90 and the microprocessor samples the incoming data to determine whether that sample is larger than the preceding sample and, if so, it is saved, with this operation being repeated on subsequent samples until it is determined that the current sample is a maximum corresponding to the peak amplitude of the impedance waveform since the last zero crossing. Likewise, the valley point is detected by testing each sample on repetitive iterations until it is determined that the current sample is a minimum value since the last zero crossing and that value is saved as well. (See block 92.) Because the algorithm must determine breathing intervals, a zero crossing technique is employed. The incoming samples are continually examined until it is detected that a sign change occurs going from positive to negative. When this happens, a zero crossing detect flag is set to TRUE. This operation is represented by decision block 94 in FIG. 4A. If a change in sign from positive to negative is not detected, control follows the path 96, the result of which will be described later.

Assuming that a negative zero crossing condition were noted at decision block 94, a test is made to determine whether the stored peak value minus the stored valley value is greater than a predetermined minimum value, nominally 0.2 ohms. This, basically, says that if the instantaneously tidal volume (peak minus valley) is not at least 0.2 ohms, the zero crossing detect flag will be reset to FALSE, effectively establishing a minimum criteria for the instantaneous tidal volume.

Assuming that the criteria is satisfied, the next operation, represented by block 98, is to compute the instantaneous tidal volume as the stored peak value minus the stored valley value. Once this instantaneous tidal volume (ITV) is computed and stored, the peak and valley detect operation 92 is effectively reset in anticipation of the detection of still further ITVs on subsequent iterations.

Figure 4B:
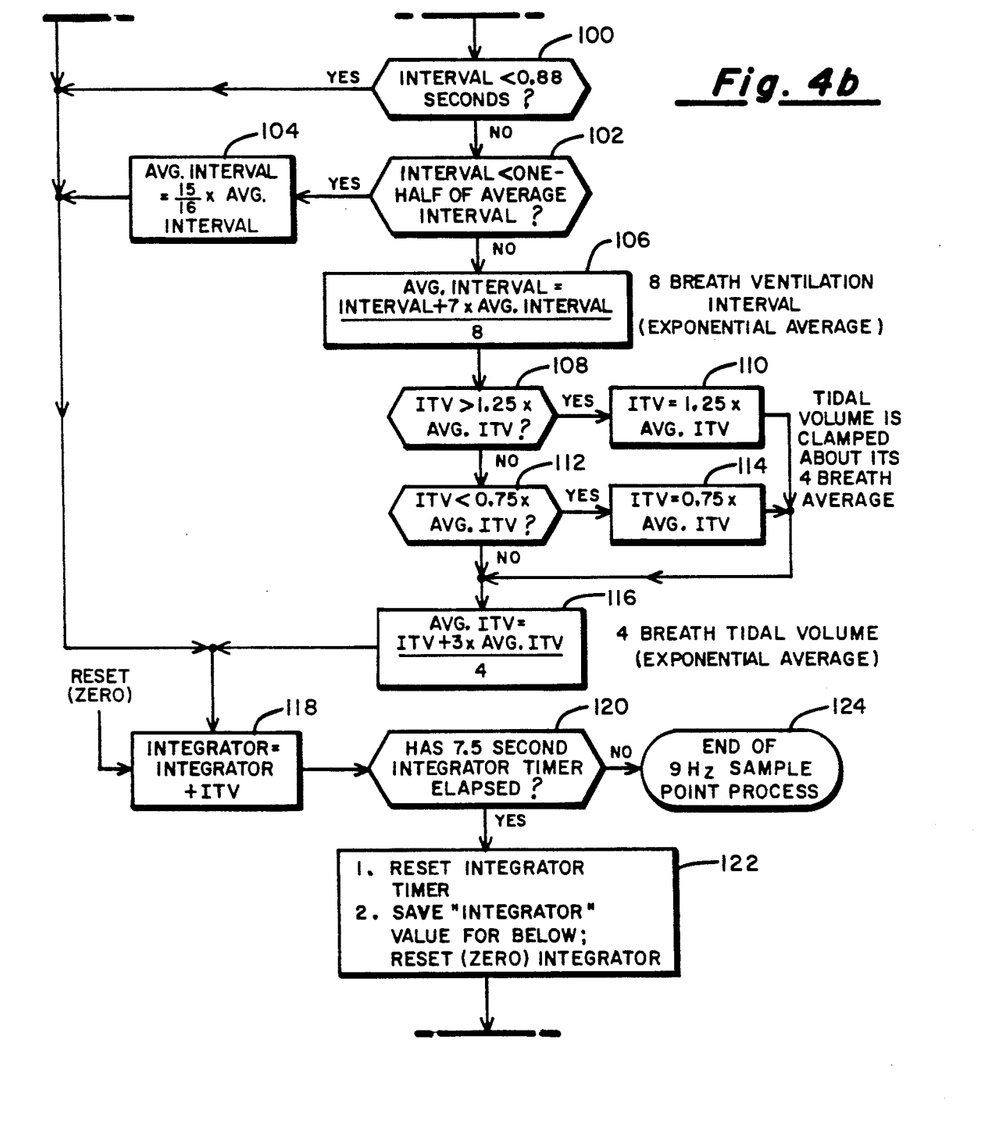

Next, referring to FIG. 4B, a test is made at decision block 100 to determine whether the time elapsed between two zero crossings, corresponding to a breath interval, is less than 0.88 seconds corresponding to 68 breaths-per-minute. Using this technique, an upper breathing rate limit is created. Detection of ITV will also be ignored if the breathing rate exceeds twice the running average breathing rate period, indicated if decision at block 102 is TRUE. Thus, a valid breath interval is not declared for purposes of tidal volume computation, and yet the average breath interval value is updated with an instantaneous breath interval value, which is half of the average interval. (In other words, twice the average breath rate). Since an 8 breath average is computed, this is equivalent to computing a new average interval as 15/16ths of the current average interval, which occurs in block 104, whereupon control passes to block 118. This noise rejection technique excludes non-steady state episodes, such as coughing or laughter, from entering into the tidal volume and ultimately minute ventilation index. Yet, if the sudden ventilatory rate increase is sustained, since the average breath interval value is always allowed to increase, this exclusionary filter will eventually allow breaths at higher rate to all be declared valid. If the current interval is found not to be less than one-half of the average interval, an eight-breath exponential average ventilation interval is computed by adding ⅛ of the current interval to ⅞ of the then-average interval. This operation is indicated by block 106 in FIG. 4B.

The instantaneous tidal volume is clamped about its four breath average. This is accomplished by first testing whether the instantaneous tidal volume computed at block 98 is greater than 1.25 times the average instantaneous tidal volume (block 108) and, if it is, setting the instantaneous tidal volume at 1.25 times the average instantaneous tidal volume (block 110). If the current ITV value is less than 0.75 times the average ITV (decision block 112), then the ITV is set at 0.75 times the average ITV (block 114).

At the completion of this clamping operation, control passes to block 116 where a four breath exponential average tidal volume is computed.

Control then exits to path 96 leading to block 118 wherein the current value of ITV is summed up with the instantaneous tidal volumes measured over a preceding predetermined time interval, e.g., 7.5 seconds. When the test reflected by decision block 120 reveals that the integration time has elapsed, the integrator is reset and the integrated value over the preceding the 7.5 seconds is stored in the microprocessor's memory (block 122). Had the decision block 120 shown that the 7.5 second interval had not expired, the processing of that sample point would be concluded and control then returns to the starting point in anticipation of the receipt of the next sample point. (See block 124).

Figure 4C:
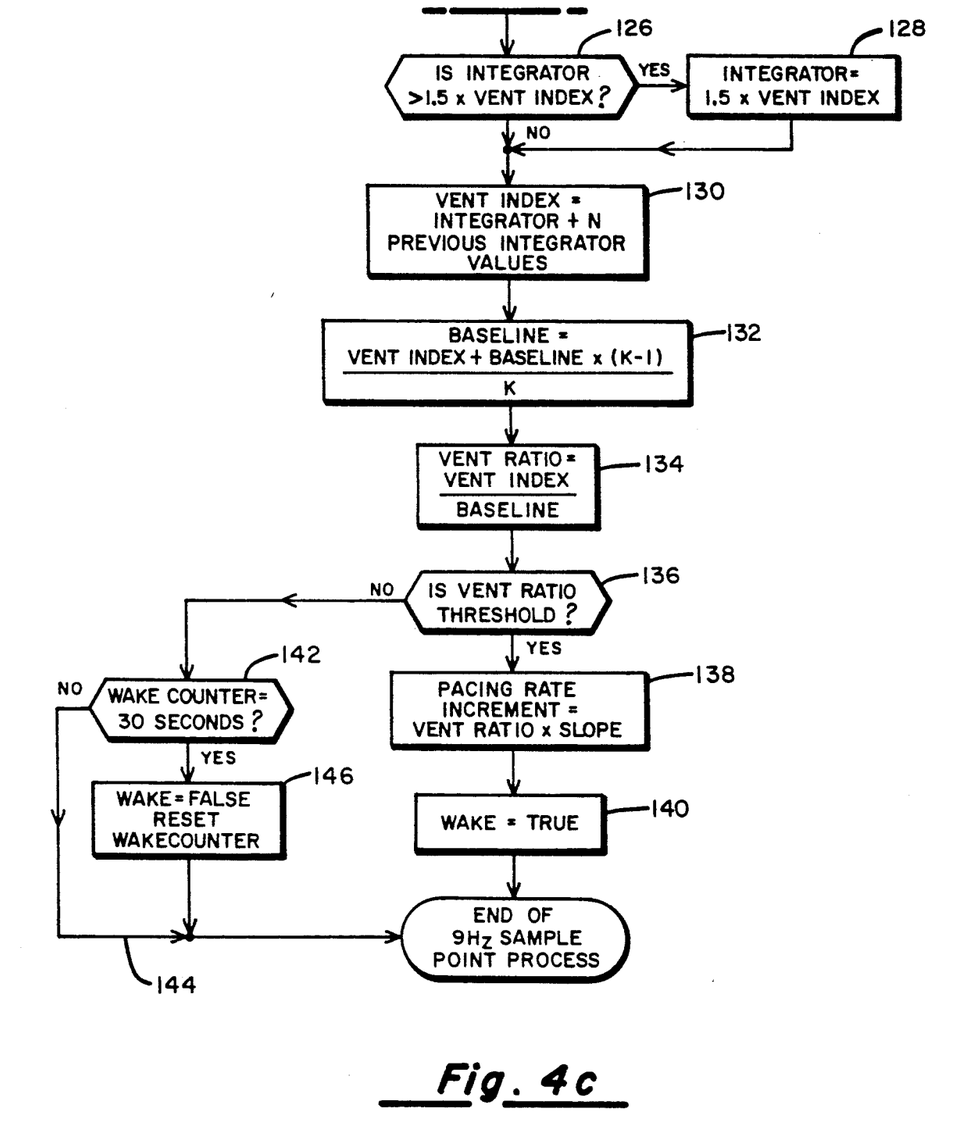

Following the operation represented by block 122, a test is made at decision block 126 to determine whether the stored integrated value exceeds 1½ times a ventilatory index value computed from the N preceding integratory cycles. If it has, it is indicative of the occurrence of noise, coughing, laughing or some other transient non-exercise ventilatory event and the integrated value is clamped at exactly 1½ times the ventilatory index (block 128). Following the test at block 126, the current ventilatory index is computed by adding the current integrated instantaneous tidal volume value with N previous integrator values, with N being a programmable constant, for example, for 4, 6 or 8, so as to yield overall integrator periods of 30, 45, or 60 seconds, respectively (block 130). Next, a baseline quantity is computed in accordance with the operation identified by in block 132. Here, the constant, K, may be programmable so as to allow variable, long-term sensor averages or baselines to be used. It is this baseline that the short term integrator value is referenced against in calculating the appropriate pacing rate. The short-term integrator value ranges between 30 and 60 seconds, depending upon the value of N chosen at the operation represented by block 130. Finally, the ventilatory ratio is computed as the ventilatory index divided by the baseline (block 134). If this ratio is determined at the decision block 136 to have exceeded a programmable threshold value, the pacing rate increment is computed as the ventilatory ratio times a slope factor (block 138). the threshold referred to is a programmable value that will disallow any rate increase until it is exceeded. The pacing rate increment is added to the base pacing rate or a lower rate limit (typically 70 bpm) to determine the actual pacing rate for the variable rate pacer pulse generator 56 in FIG. 1. The slope referred to is also a programmable value that allows the physician to adjust the pacing rate increase for a given level of ventilatory increase.

Following the computation of the pacing rate increment, the "wake" flag is set equal to true (block 140) prior to the end of the current 9 Hz sample point processing. As mentioned above, the "wake" flag disables the "sleep" mode when est to TRUE. When the ventilatory level is below threshold, it will be set to FALSE, enabling the "sleep" mode, which shuts off the impedance sensor and signal processing circuitry for a predetermined time interval, e.g., 30 seconds. Had the test at decision block 136 revealed that the ventilatory ratio had not been greater than the threshold, control would have passed to the decision block 142 to determine whether the "wake" counter had reached 30 seconds. If not, control passes over path 144 and the processing of the current sample point terminates. Had the "wake" counter 142 reached its 30 second count, the "wake" flag would have been set to FALSE and the "wake" counter reset to "0" (block 146) before ending the processing of the current sample point.

Persons skilled in the art having the flow chart and the source code for the software illustrated in FIGS. 4A through 4C are in a position to write object code executable by the microprocessor controller and, hence, it is unnecessary to include herein the detailed object code. The appendix comprises pseudo-code written so as t facilitate C-language implementation.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. More particularly, in spite of the fact that essentially the entire algorithm, including the adaptive filter, the zero-crossing detection, peak detection, etc., and the control is described as a digital (microprocessor) implementation, those skilled in the art appreciate that an analog implementation and/or sampled data (switched capacitor or switched current) implementation is also possible.

APPENDIX

MV PI ALGORITHM
Integer Version with Sleep Mode

Revision 4.0 - Control for 3 stage filter; remove coasting (rolloff)
Revision 4.1 - Correction: removal of rolloff flag from ITV pruning
   9/29/92

{} = comments
The scope of a conditional statement includes successively indented instructions.

INPUTS:

| | |
|---|---|
| * | starred variables below are programmable |
| SP | sample point value (@ 9 Hz rate) from A/D |
| RRinterval | most recent cardiac cycle length |

Systole                flag indicating new cardiac cycle

COMPUTATIONAL VARIABLES:

| Name | Range (bits) | Description |
|---|---|---|
| Detect | 1 | zero crossing detect flag |
| Peak | 8 | peak detector maximum value |
| Valley | 8 | peak detector minimum value |
| ITV | 8 | instantaneous (single breath) tidal volume |
| AvgTV | 10 | average (four breath exp.) tidal volume, shifted up 2 |
| # Integ | 11 | tidal volume integrator |
| PrevSP | 8 | save value for sample point (previous SP) |
| VentI | 8 | instantaneous ventilatory (breath) interval |
| # AvgVentI | 16 | average (8 breath exp.) ventilatory interval, shifted up 8 |
| AllowedVentI | 8 | limit of instantaneous ventilatory interval |
| Vtimer | 8 | timer for ventilatory interval |
| Itimer | 8 | timer for integration period |
| # Filt | 2 | adaptive filter indicator (0=Lo,1=Med,2=Hi) |
| SetFilt | 2 | value to set Filt at end of integration period |
| AvgCCycle | 12 | average (16 beat exp.) cardiac cycle, shifted up 4 |
| # MVz | 11 | minute ventilation index |
| * N | 3 | number of 7.5 second integrations summed (nominally 6, which = 45 seconds) |
| # MVzbl | 16 | baseline value, shifted up 5 (* 32) from MVz |
| * KBL | 6 | baseline-MVz sub-sampling value (nom 32 : 2 hours; 16 : 1 hour, 8 : 30 min, 4 : 15 min) |
| Nbl | 6 | counter for baseline sub-sampling |
| MVratio | ** | ratio of current MV index to the baseline |
| * Thresh | ** | threshold above baseline at which rate response begins |
| * SensorGain | 6 | sensor to heart rate gain factor |
| MAXVALUE | 8 | suitable maximum reset value (eg. 255 in 8 bit system) for valley detector |
| SLEEPMODE | 1 | flag indicating 50 % duty cycle sleep mode |
| WAKE | 1 | flag indicating wake phase when sleep mode active |
| sleepcounter |  | 30 second counter (may be handled by sampling existing counters; resolution not critical |
| timereset | 1 | flag to reset mv timers after wake up |
| numperiods | 8 | counter for number of 7.5 second periods to reach min 30 sec ON period in sleep mode |
| drive_rate | 8 | raw MV sensor rate output |
| lastrate | 8 | saved (previous cycle) sensor rate |

** managed with look up tables in Research integer code implementation

OUTPUTS:

| | |
|---|---|
| SensorRate | MV sensor rate (referenced from LRL) value |
| # | pound variables above should output to prog. register |

CARDIAC CYCLE BASED PROCESSES

Avg Cardiac Cycle
{ Systole set by main process for either paced or sensed beat }

IF Systole = TRUE THEN
    { calculate initial RRinterval with at least 10 ms resolution, eg. from 146 Hz timer }

IF RRinterval > AvgCCycle * 1.1 THEN
        RRinterval = AvgCCycle * 1.1
    IF RRinterval < AvgCCycle * 0.9 THEN
        RRinterval = AvgCCycle * 0.9
    AvgCCycle = (RRinterval + AvgCCycle * 7)/8

Sensor Rate {calculates rate increment to be added to LRL in main process }

IF (drive_rate - lastrate) > 2 THEN
    SensorRate = lastrate + 2
    ELSE IF (drive_rate - lastrate) < -2 THEN
        SensorRate = lastrate - 2
        ELSE SensorRate = drive_rate
        lastrate = SensorRate
IF drive_rate = 0 AND numperiods > 3 THEN
    WAKE = FALSE

SLEEP MODE MANAGEMENT

IF SLEEPMODE = TRUE THEN
    IF WAKE = FALSE THEN
        increment sleepcounter

```
IF sleepcounter > 30 seconds OR IF ( accelerometer wakeup ) THEN
        WAKE = TRUE
        sleepcounter = 0
        timereset = TRUE
```

IF WAKE = TRUE OR SLEEPMODE = FALSE :
BEGIN MV 9.125 Hz Sample Point Process:
(enter every 1/9.125 seconds)

TIMERS
```
IF timereset = TRUE
        Vtimer = 0
        Itimer = 0
        timereset = FALSE
        numperiods = 0
Increment Vtimer
Increment Itimer
```

FILTER SWITCH CRITERIA (One and only one of three XXFilt flags must be true, and either none or one of the SetXXFilt flags will be TRUE )

```
IF Filt = 0 THEN
        IF AvgVentI < 2.6 seconds AND AvgCCycle < 0.75 seconds THEN SetFilt = 1
                ( 22 VPM ...           80 BPM )
IF Filt = 1 THEN
        IF AvgVentI > 3.0 seconds OR AvgCCycle > 0.769 seconds THEN SetFilt = 0
                ( 20 VPM ...           78 BPM )
        IF SetFilt != 0 THEN IF AvgCCycle < 0.625 seconds THEN SetFilt = 2
                (                      96 BPM )
IF Filt = 2 THEN
        IF AvgVentI > 3.0 seconds OR AvgCCycle > 0.638 seconds THEN SetFilt = 1
                ( 20 VPM ...           94 BPM )
```

PEAK DETECTOR

```
IF SP > Peak THEN
        Peak = SP
IF SP < Valley THEN
        Valley = SP
```

ZERO CROSS DETECTOR

```
IF SP < 0 AND PrevSP > 0 THEN
        Detect = TRUE
PrevSP = SP
```

ITV CALCULATION with AMPLITUDE BASED DETECT ABORT CRITERION

```
IF Detect = TRUE THEN
        ITV = Peak - Valley
        IF ITV < 200 milliohms THEN       ( Minimum required amplitude )
                Detect = FALSE
```

VENT INTERVAL CALCULATION with VENT RATE BASED DETECT ABORT CRITERION

```
IF Vtimer > 12 seconds THEN      ( Force 5 VPM minimum breath rate )
        Detect = TRUE IF Vtimer < 0.877 seconds THEN
        Detect = FALSE           ( Upper limit = 68 VPM )

IF Detect = TRUE THEN
        VentI = Vtimer
        Vtimer = 0
        AllowedVentI = AvgVentI/2
        IF VentI < AllowedVentI THEN
                Detect = FALSE
                AvgVentI = (AllowedVentI + 7 * AvgVentI)/8     (8 breath exp avg)
```

ELSE AvgVentI = (VentI + 7 * AvgVentI)/8

IF Detect = TRUE THEN

ITV PRUNING and AvgITV CALCULATION, with ITV Hold during Filter Rolloff

IF AvgTV > 200 milliohms AND ITV > 1.25 * AvgTV THEN ITV = 1.25 * AvgTV
IF AvgTV > 200 milliohms AND ITV < 0.75 * AvgTV THEN ITV = 0.75 * AvgTV

AvgTV CALCULATION AND RESET PEAK DETECTOR AND BREATH DETECT FLAG

AvgTV = (ITV + 3 * AvgTV)/4      { 4 breath exp avg }
Peak = 0
Valley = MAXVALUE
Detect = FALSE

INTEGRATE PEAKS

Integ = Integ + ITV

TEST and PROCESS IF END of INTEGRATION PERIOD

IF ITimer > 7.5 Seconds THEN
    ITimer = 0
    Increment numperiods

MANAGE FILTER FLAGS

Filt = SetFilt

PRUNE Integ

IF MVz > 1.6 Ohms/Minute        {ie. MVz > 1.6 Ohms/min * 7.5/60 min * X Counts/Ohm, or
                                 MVz > 0.20 * X Counts/Ohm}
    IF Integ > 1.5 * MVz AND AvgVentI < 7.5 seconds THEN
        Integ = 1.5 * MVz

MV INDEX CALCULATION

MVz = (Integ + Sum of N-1 Previous Integs)/N
{Save Integ along with N-2 Previous Integs for next time}
Integ = 0

BASELINE CALCULATION

Increment Nbl
IF Nbl = KBL THEN
    MVzbl = MVzbl + MVz - (MVzbl >> 5)
    Nbl = 0

MV RATIO CALCULATION

IF MVbl > 1.1 Ohms/Minute THEN
    MVratio = MVz/MVbl
    ELSE MVratio = 1

SENSOR DRIVE RATE CALCULATION

IF MVratio > (1 + Thresh) THEN
    drive_rate = (MVratio - 1) * SensorGain
    ELSE drive_rate = 0;
RETURN

What is claimed is:
1. A rate-adaptive cardiac rhythm management device including:
(a) means for sensing trans-thoracic impedance variations in a patient due to respiratory and cardiac activity;
(b) variable rate pulse generator means for stimulating said patient's heart;
(c) means for deriving from said sensed impedance variations a control signal proportional to the patient's minute ventilation, said pulse generator being connected to receive said control signal for varying the rate at which the stimulation occurs between a lower rate limit and an upper rate limit, with said means for deriving said control signal having (i) analog-to-digital converter means coupled to receive an analog signal corresponding to said trans-thoracic impedance variations due to respiratory and cardiac activity for converting same to a serial digital signal train, (ii) a digital filter having an input connected to receive said digital signal train and an output, said filter operating to attenuate components to said signal train due to cardiac activity over a range of heart rates and respiratory rates while passing components in said signal train due to respiratory activity, (iii) peak detecting means coupled to said output of said digital filter for locating the maximum and minimum values of said components in said signal train due to respiratory activity, (iv) tidal volume determining means responsive to said peak detecting means for determining the patient's instantaneous tidal volume and average tidal volume over a predetermined number of breathing cycles, (v) ventilatory index determining means responsive to said tidal volume determining means for summing said average tidal volumes over a predetermined time interval, yielding said ventilatory index, (vi) means for establishing a baseline value by computing the exponential average of said ventilatory index over a time interval that is long compared to said predetermined time interval, (vii) means for computing a ventilatory ratio as the quotient of said ventilatory index and said baseline value, and (viii) means for adding a pacing rate increment to said lower rate limit, said increment being the product of said ventilatory ratio and a predetermined constant.

2. The rate adaptive cardiac rhythm management device as in claim 1 and further including a microprocessor-based controller programmed to repeatedly compare the output from said digital filter on a given cycle with the output of said digital filter on an immediately preceding cycle to determine said maximum and minimum values and for subsequently storing only said maximum and minimum values.

3. The rate adaptive cardiac rhythm management device as in claim 2 wherein said microprocessor-based controller includes means for subtracting said minimum value from said maximum value to obtain said instantaneous tidal volume.

4. The rate adaptive cardiac rhythm management device as in claim 1 wherein said tidal volume determining means include means for limiting said instantaneous tidal volume to a predetermined percentage of said average tidal volume.

5. The rate adaptive cardiac rhythm management device as in claim 1 and further including means for periodically activating said means for sensing trans-thoracic impedance variations from a "sleep" state and for deactivating said means for sensing trans-thoracic impedance variations when said ventilatory ratio falls below a preprogrammed threshold value.

6. The rate adaptive cardiac rhythm management device as in claim 1 and further including means responsive to said trans-thoracic impedance variations for determining an average breathing rate over a predefined time interval.

7. The rate adaptive cardiac rhythm management device as in claim 6 wherein said digital filter comprises an adaptive, four-pole, elliptic filter having a plurality of weighting input sets, said weighting input sets being chosen as a function of said breathing rate and the patient's heart rate.

8. The rate adaptive cardiac rhythm management device as in claim 7 wherein said adaptive, four-pole elliptic filter includes decimation means for converting the pulse rate frequency of said serial digital signal train to a predetermined lower frequency.

9. The rate adaptive cardiac rhythm management device as in claim 6 and further including means for determining the patient's instantaneous breathing rate and means for determining whether said instantaneous breathing rate exceeds said average breathing rate by a predetermined percentage whereby said breath whose instantaneous rate is high compared to said average breathing rate is precluded from being processed by said ventilatory index determining means.

* * * * *